(12) United States Patent
Heremans et al.

(10) Patent No.: US 6,810,717 B2
(45) Date of Patent: Nov. 2, 2004

(54) METHOD FOR DETERMINING ENGINE LUBRICATING OIL CONDITION

(75) Inventors: Joseph Pierre Heremans, Troy, MI (US); Su-Chee Simon Wang, Troy, MI (US)

(73) Assignee: Delphi Technologies, Inc., Troy, MI (US)

( * ) Notice: Subject to any disclaimer, the term of this patent is extended or adjusted under 35 U.S.C. 154(b) by 64 days.

(21) Appl. No.: 10/384,866

(22) Filed: Mar. 10, 2003

(65) Prior Publication Data

US 2004/0177677 A1 Sep. 16, 2004

(51) Int. Cl.⁷ .................. G01N 11/00; G01N 25/18; G01N 33/26
(52) U.S. Cl. .................. 73/53.05; 73/54.01; 73/54.02; 73/54.42
(58) Field of Search ................ 73/54.01, 54.02, 73/53.05, 54.42

(56) References Cited

U.S. PATENT DOCUMENTS

| | | | | |
|---|---|---|---|---|
| 3,753,369 A | * | 8/1973 | Fowler et al. | 374/54 |
| 4,007,629 A | * | 2/1977 | Hochstein | 73/53.05 |
| 5,038,295 A | * | 8/1991 | Husband et al. | 702/34 |
| 6,158,381 A | * | 12/2000 | Bray | 116/216 |
| 6,509,749 B1 | | 1/2003 | Buelna et al. | |
| 6,535,001 B1 | | 3/2003 | Wang | |
| 6,557,396 B2 | | 5/2003 | Ismail et al. | |
| 6,575,018 B2 | | 6/2003 | Berndorfer et al. | |
| 6,590,402 B2 | | 7/2003 | Wang et al. | |

OTHER PUBLICATIONS

Krishnamoorthy, P. R. et al., "Effect of Antioxidants and Metal Deactivator on the Oxidation of Transformer Oil", IEEE Transactions on Electrical Insulation, vol. 27, No. 2, Apr. 1992, pp. 271–277.*

* cited by examiner

*Primary Examiner*—Daniel S. Larkin
(74) *Attorney, Agent, or Firm*—Jimmy L. Funke

(57) ABSTRACT

Activation energy, W, is determined from oil conductivity measurements to thereby provide engine oil condition from a known relationship between viscosity and W. Changes of W at a given temperature as the oil ages are reflective of changes in viscosity of the oil at the same given temperature, wherein changes in W at different temperatures are reflective of changes of viscosity at those respective temperatures as the oil ages. To determine viscosity, the temperature dependence of the oil's conductivity is measured to deduce the value of W at a given temperature. W is monitored as the oil ages. W may also be determined through the ratio of the oil conductivities at two different temperatures by techniques well known in the art by which the viscosity may be determined as the oil ages.

16 Claims, 2 Drawing Sheets

METHOD FOR DETERMINING ENGINE LUBRICATING OIL CONDITION

TECHNICAL FIELD

The present invention relates to a method for determining engine oil condition from knowledge of its activation energy derived from measurements of its conductivity.

BACKGROUND OF THE INVENTION

Three of the important properties of an internal combustion engine lubricating oil, herein simply referred to as "oil", that are worth sensing are the viscosity, the condition of the additive package, and the total acidity of the oil. Lubricating oil used in internal combustion engines for lubrication of moving components deteriorates by the depletion of the additives and the increase in the acidity of the oil, as measured by a quantity called the total acid number (TAN). The depletion of the additives and the increase in the acidity of the oil, in some combination, are sensed in gasoline engines by measuring the electrical conductivity of the oil. As the additive package varies from oil to oil, it has proven necessary to monitor the actual variation of the electrical conductivity of each particular oil filling as it ages in the engine. Oil in diesel engines is degraded by the same mechanisms as in gasoline engines, but with the additional presence of soot particles, which increases as the oil ages. During usage of a diesel engine, the crankcase oil gradually builds up soot which is a combustion product in the combustion chamber of the engine and which is transferred in small amounts to the crankcase oil. When the soot builds up to an unacceptable amount, say about four percent by mass or weight of the oil, the lubricating quality of the oil is inhibited. Thus, it is necessary to change the crankcase oil whenever the soot content reaches an unacceptable value.

The prior art also describes a number of techniques that measure the dielectric constant with a sensor built like a capacitor. The capacitor like sensor includes two metal electrodes with the lubricating oil acting as the dielectric between the electrodes. The two metal electrodes take the form of two parallel plates or two concentric cylinders. Most of these sensors determine the permittivity of the oil through a measurement of the capacitance between the metal electrodes. Sensors that measure the loss tangent, essentially the ratio of the electrical conductivity of the oil to the dielectric constant, have also been proposed Delphi Corporation possesses a design for a gasoline engine oil contaminants sensor that measures the electrical conductivity of the oil using D.C. or a low frequency (below one kHz). The sensor consists of two metal electrodes, which can be parallel plates or concentric cylinders or rings. The conductivity is determined through a measurement of the electrical resistance between the electrodes. This sensor mainly detects the changes in the concentration of ions in the oil. In this regard, fresh oil is slightly basic. As the oil ages, the combustion products create acidic ions in the oil. At first, the acids neutralize the bases and the conductivity decreases. As the oil ages further, the increase in acidic ions makes the conductivity rise again. This makes for a very good oil quality sensor in gasoline engines.

Delphi Corporation also possesses a method that measures the electrical conductivity of diesel engine oil at high frequencies (one MHz to ten MHz) to determine soot concentration utilizing a sensor having the same geometry as the D.C. sensor for gasoline engines as described above and can be used to measure the electrical conductivity of diesel engine oil using D.C. or low frequencies (below one kHz).

It is also known in the art that the viscosity of internal combustion engine oils increases as the oil ages. Internal combustion engine oil condition can, therefore, be determined by monitoring the viscosity of the oil. The prior art describes a number of techniques for the measurement of viscosity in engine oil utilizing viscosimeters. Most viscosimeters are based on a measurement of the shear force associated with the displacement of the oil. In order to make viscosity measurements of oil on operating vehicles, it is necessary to provide a measuring system which is sufficiently inexpensive to incorporate on automotive vehicles made in large numbers and sufficiently rugged to withstand the engine operating environment. Moreover, a method of measuring viscosity must be valid for many types of oil, both natural and synthetic, and containing many different types of additives.

It would be more economical to an engine/automotive manufacturer to use existing oil quality sensors based on the electrical conductivity of the oil to somehow use this quantity as an indication of the oil viscosity than to measure the viscosity using existing viscosimeters based upon a shear force measurement of the oil.

Accordingly, what is needed in the art is a more robust method to determine oil condition utilizing an indication of oil viscosity which is independent of the brand of oil.

SUMMARY OF THE INVENTION

The present invention is a method by which the condition of internal combustion engine oil is determined using electrical conductivity measurements of the oil at, preferably, D.C. or low frequencies (that is, frequencies less than two kHz).

According to the method of the present invention, an activation energy can be determined from oil conductivity measurements which is related to the oil viscosity. Changes of the activation energy at a given temperature as the oil ages are reflective of changes in viscosity of the oil at the same given temperature, wherein changes in the activation energy at different temperatures are reflective of changes of viscosity at those respective temperatures as the oil ages.

As a result, to provide an indication of viscosity or changes in viscosity of oil as it ages, it is possible to simply measure the temperature dependence of the oil's conductivity, deduce the value of the activation energy at a given temperature and monitor the activation energy as the oil changes, wherein the activation energy is related to the viscosity at a given temperature. The activation energy may also be determined through the ratio of the conductivities at two different temperatures by techniques well known in the art by which the viscosity may be determined as the oil ages.

It is, therefore, possible to determine the condition of internal combustion engine oil by monitoring the value or change in value of the activation energy thereby determining when the oil should be replaced with fresh oil.

Accordingly, it is one object of the present invention to measure the electrical conductivity of engine oil at DC or low frequencies to determine the activation energy thereof.

This and additional objects, features and advantages of the present invention will become clearer from the following specification of a preferred embodiment.

DESCRIPTION OF THE PREFERRED EMBODIMENT

Figure 1:
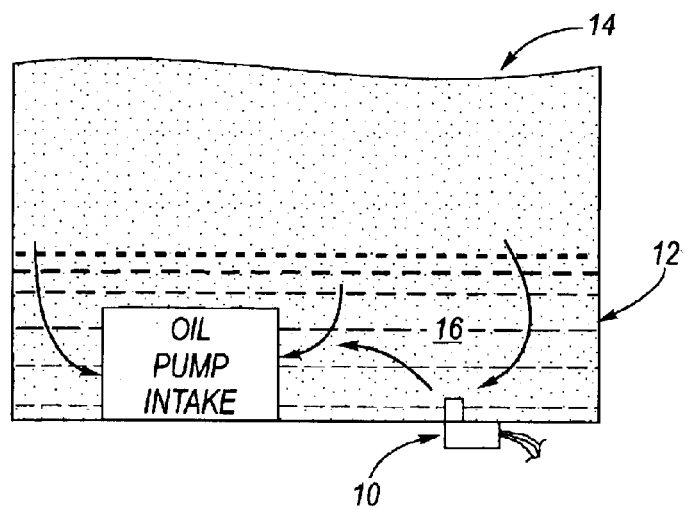
FIG. 1 is a schematic view of an engine environment in which the method of the present invention may be typically used.

It is well known in the art that the electrical conductivity S of a fluid is given by:

$$S = Nqu \quad (1)$$

where N is the density of the charge carrying species, typically ions in engine oils, q is the electric charge of each ion, typically on the order of the electron charge $1.6 \times 10^{-19}$ Coulomb, and u is the mobility of the species. The mobility u is defined as the ion group velocity v under an applied electric field E and is given by:

$$u = v/E \quad (2).$$

In electrolytes the mobility u is directly related to the viscosity $\eta$. This is understood by considering the motion of an ion of charge q under an electric field E. This ion, of radius r is accelerating under a force F:

$$F = qE \quad (3).$$

This ion motion is analogous to that of a classical Hoeppler viscosity meter, well know in the art, that uses a ball of mass m and diameter D dropping in a viscous fluid under the gravitational force mg where g is the acceleration due to gravity 9.8 m/s². The ball drops at a velocity inversely proportional to the viscosity. Therefore, the mobility u is also inversely proportional to the viscosity (see W. J. Moore, Physical Chemistry, 4$^{th}$ edition, Longmans-Green and Co. Ltd, Prentice-Hall Inc. 1962) by which:

$$u = q/(6\pi r \eta) \quad (4).$$

Unfortunately, as the oil ages, the number of ions N and their charge q, which depends on their ionization state, change along with changes in viscosity. Therefore, the electrical conductivity S is not a straightforward measure of viscosity.

As is also well known in the art, the viscosity of most fluids varies with temperature and the temperature dependent viscosity $\eta(T)$ can be expressed as:

$$\eta(T) = \eta_0 e^{-(W/(RT))} \quad (5)$$

where R is the ideal gas Boltzmann constant (8.314 joules/[mole K]), W (joules/mole) is the activation energy, T is temperature (K), and $\eta_0$ is a first arbitrary constant. The activation energy W can be viewed as the energy needed for one charge carrying particle to move from molecule to molecule as it is being dragged through the fluid and is on the order of one-third to one-half of the heat of vaporization (see W. J. Moore, Physical Chemistry, 4$^{th}$ edition, Longmans-Green and Co. Ltd, Prentice-Hall Inc. 1962). In a fluid consisting mostly of hydrocarbon species, it is known in the art that the heat of vaporization is related to the molecular weight of the fluid which, in turn, is related to the viscosity. Therefore, an increase in the activation energy W is related to an increase in the viscosity. It is expected that if W can be measured independently of N, changes of W at a given temperature as the oil ages are reflective of changes in viscosity of the oil at the same given temperature wherein changes in W at different temperatures are reflective of changes of viscosity at those respective temperatures as the oil ages. Hence, the activation energy W is an indication of the viscosity of the oil. Since it is unlikely that the density N has a large temperature dependence, it is expected from equations 1 and 5 that the temperature dependent electrical conductivity S(T) can be expressed as:

$$S(T) = S_0 e^{-(W/(RT))} \quad (6)$$

where $S_0$ can be expressed as:

$$S_0 = Nq^2/6\pi r \eta_0 \quad (7)$$

and wherein $S_0$ may be treated as a second arbitrary constant.

As a result, to determine an indication of the viscosity or changes in the viscosity of oil as it ages, it is possible to simply measure the temperature dependence of the oil's conductivity, deduce the value of W at a given temperature through equation 6 and monitor W as the oil changes wherein W is related to the viscosity as previously described. The activation energy W may also be determined through the ratio of the conductivities at two different temperatures by equation 6 by techniques well known in the art, yielding:

$$W = (R((T_1)^{-1} - (T_2)^{-1})^{-1})(\ln(S(T_2)/S(T_1)) \quad (8)$$

wherein $T_1$ and $T_2$ are mutually close in value.

Most oils have viscosity index improvers in their additive package that are activated at higher temperatures to increase the high temperature viscosity above that determined by equation 5. Therefore, the temperatures selected for the present invention must be such as to avoid the activation of the viscosity index improvers within the oil. Suggested temperatures for the present invention are $T_1 = 40$ degrees Celsius and $T_2$ 60 degrees Celsius.

Referring now to the drawings, FIG. 1 depicts an environment of placement and operation of an engine oil viscosity sensor 10. The sensor 10 is located at the bottom of an oil pan 12 of an internal combustion engine 14. In operation of the sensor 10, which sensor construction is known in the prior art, oil 16 in the oil pan 12 is sloshed, causing the oil to flowably fill a space inside the sensor. As a result, the conductivity of the oil in the space (between electrodes of the sensor) changes over time as the oil ages with hours of operation of the engine.

Figure 2:
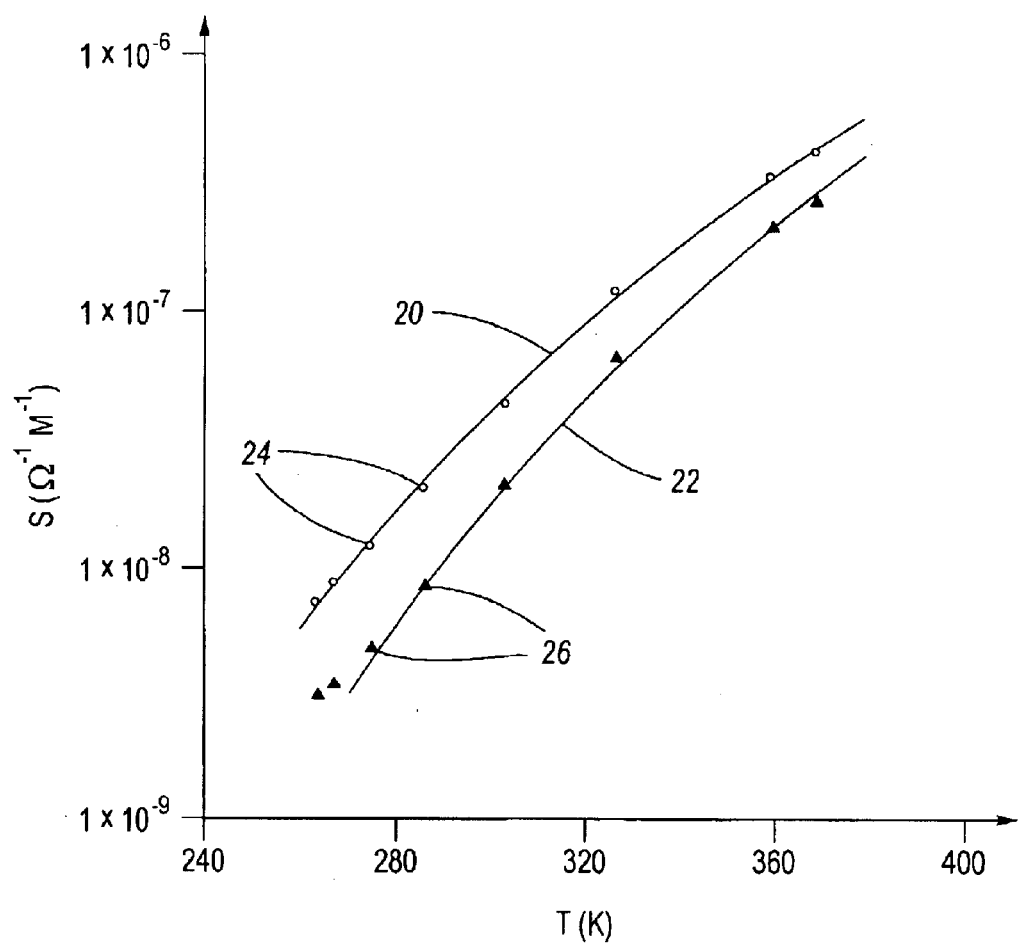
FIG. 2 is a first plot of conductivity versus temperature of a first selected oil.

FIG. 2 depicts a first plot 20 of conductivity versus temperature of a first diesel engine lubricating oil in a fresh condition and a second plot 22 of conductivity versus temperature of the first diesel engine lubricating oil, now in an aged condition (19,973 km), wherein the plots 20, 22 are obtained from equation 6 and the points 24, 26 are sensor data. In both plots 20, 22, the oil is TPM4596 15W-40 in a Renault Kangoo diesel engine.

Figure 3:
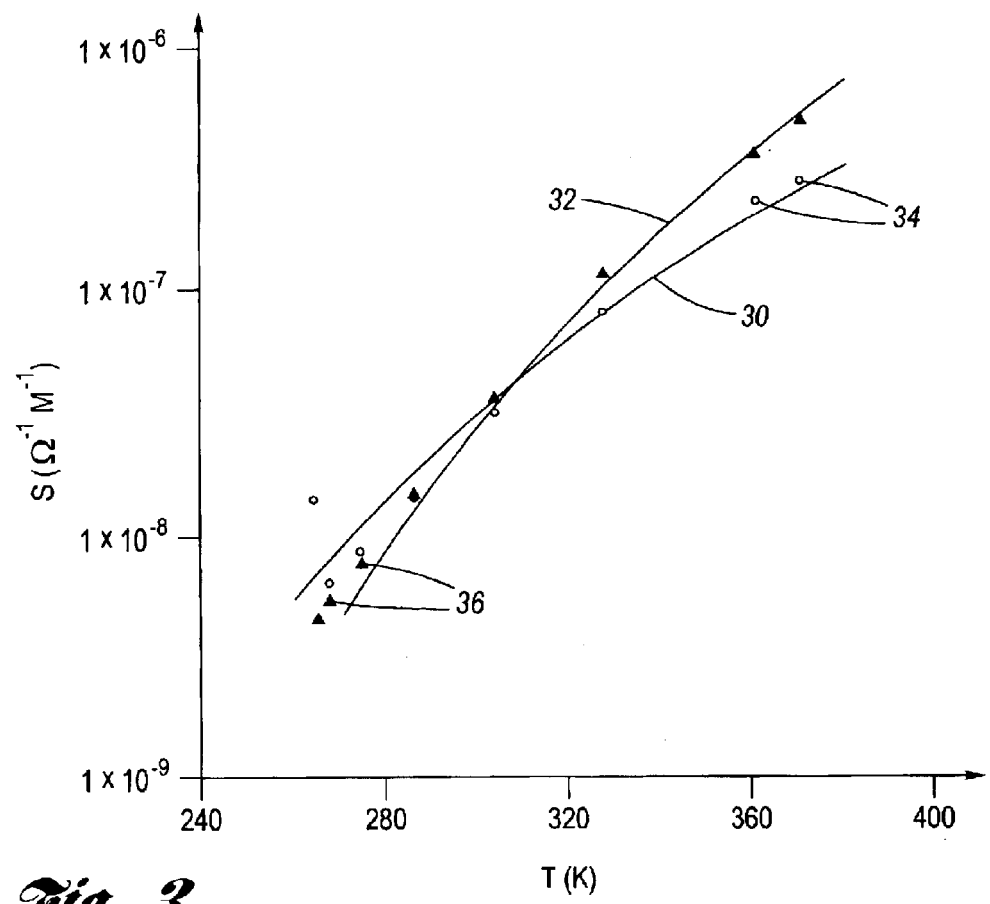
FIG. 3 is a second plot of conductivity versus temperature of a second selected oil.

FIG. 3 depicts a first plot 30 of conductivity versus temperature of a second diesel engine lubricating oil in a fresh condition and a second plot 32 of conductivity versus temperature of the second diesel engine lubricating oil, now in an aged condition (15,202 km), wherein the plots 30, 32 are obtained from equation 6 and the points 34, 36 are sensor data. In both plots 30, 32 the oil is Mobil Delvac MX 15W-40 in a Renault Megane diesel engine.

Figure 4:
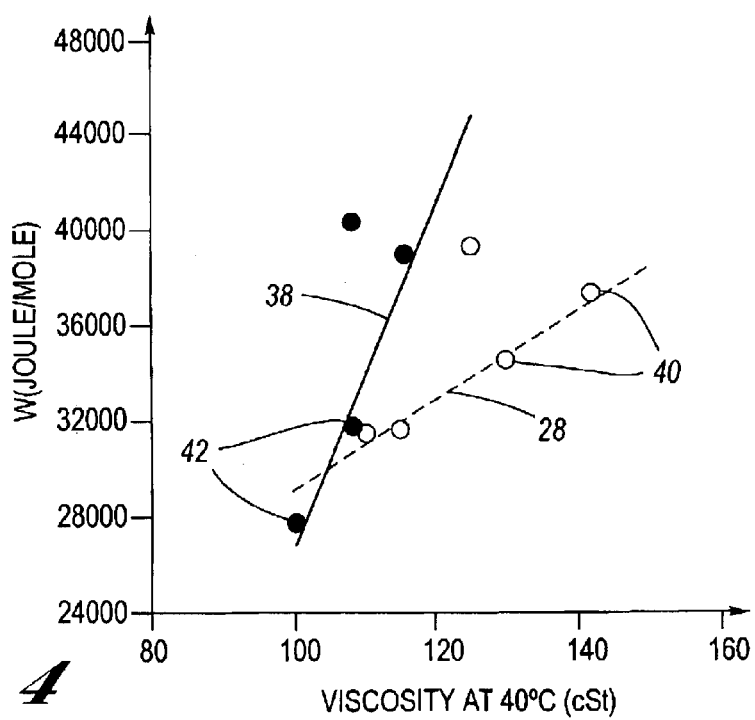
FIG. 4 is a plot of activation energy versus viscosity for the first and second selected oils.

FIG. 4 is a pair of plots 28, 38, of activation energies derived from FIGS. 2 and 3, respectively, through equation 6 versus measured viscosity at a temperature of 40 degrees Celsius, wherein the points 40, 42 are sensor data. The variation of activation energies with viscosity is apparent in FIG. 4.

It is, therefore, possible to determine the condition of internal combustion engine oil by monitoring the value or change in value of the activation energy W, thereby determining when the oil should be replaced with fresh oil. For example, if W reaches or exceeds a value (threshold), for instance, of 40,000 Joule/mole then the oil should be replaced with fresh oil or, if a change in W of, for example, a sixty per cent increase from the value of W when the oil was fresh (i.e. from 28,000 to about 44,000 Joule/mole) occurs then the oil should be replaced with fresh oil.

To those skilled in the art to which this invention appertains, the above described preferred embodiment may be subject to change or modification. Such change or modification can be carried out without departing from the scope of the invention, which is intended to be limited only by the scope of the appended claims.

What is claimed is:

1. A method for determining engine lubricating oil condition comprising the steps of:
   determining a relationship between condition of the oil and viscosity of the oil;
   determining a relationship between activation energy of the oil and viscosity of the oil;
   measuring temperature dependent conductivity, S(T) of a selected oil over a predetermined range of temperatures;
   calculating an activation energy, W, of the oil at a selected temperature responsive to said step of measuring; and
   determining the condition of the oil from the relationships between activation energy, viscosity, and condition.

2. The method of claim 1, wherein said step of measuring is performed at a low frequency between zero Hz and substantially two KHz.

3. The method of claim 1, wherein said step of calculating comprises calculating W from a relation:

$$S(T) = S_0 e^{-(W/(RT))}$$

wherein $S_0$ is a first constant, R is Boltzmann's constant, and T is Kelvin temperature.

4. The method of claim 3, wherein said step of measuring is performed at a low frequency between zero Hz and substantially two KHz.

5. The method of claim 4, wherein said predetermined range of temperatures is selected such that any viscosity index improver in said oil is inactive.

6. The method of claim 5, further comprising periodically repeating said steps to thereby determine the condition of the oil as the oil ages.

7. The method of claim 6, further comprising detecting a preselected oil condition based upon W attaining a predetermined threshold value.

8. The method of claim 6, further comprising detecting a preselected change in oil condition based upon a predetermined change in W.

9. A method for determining properties of engine oil, comprising the steps of:
   determining a relationship between condition of the oil and viscosity of the oil;
   determining a relationship between activation energy of the oil and viscosity of the oil;
   measuring temperature dependent conductivity, $S(T_1)$ of a selected oil at a first predetermined temperature, $T_1$;
   measuring temperature dependent conductivity, $S(T_2)$ of a selected oil at a second predetermined temperature, $T_2$;
   calculating an activation energy, W, of the oil from a ratio of the conductivities of the oil obtained from said first and second steps of measuring; and
   determining condition of the oil from the relationships between activation energy, viscosity, and condition.

10. The method of claim 9, wherein the first and second steps of measuring is performed at a low frequency between zero Hz and substantially two KHz.

11. The method of claim 9, wherein said step of calculating comprises calculating W from a relation:

$$W = (R((T_1)^{-1} - (T_2)^{-1})^{-1})(\ln(S(T_2)/S(T_1)))$$

wherein R is Boltzmann's constant, and $T_1$ and $T_2$ are Kelvin temperature.

12. The method of claim 11, wherein said step of measuring is performed at a low frequency between zero Hz and substantially two KHz.

13. The method of claim 12, wherein the first and second temperatures are preselected so that any viscosity index improver present in said oil is inactive.

14. The method of claim 13, further comprising periodically repeating said steps to thereby determine the condition of the oil as the oil ages.

15. The method of claim 14, further comprising detecting a preselected oil condition based upon W attaining a predetermined threshold value.

16. The method of claim 14, further comprising detecting a preselected change in oil condition based upon a predetermined change in W.

* * * * *